United States Patent [19]

Butterworth et al.

[11] 4,081,582

[45] Mar. 28, 1978

[54] FIBROUS MATERIAL AND METHOD OF MAKING THE SAME

[75] Inventors: George A. M. Butterworth, Western Springs; Robert T. Elias, Downers Grove; Wayne D. Miller, Oak Lawn, all of Ill.

[73] Assignee: Johnson & Johnson, New Brunswick, N.J.

[21] Appl. No.: 734,208

[22] Filed: Oct. 20, 1976

[51] Int. Cl.² .............................................. B32B 5/08
[52] U.S. Cl. .................................. 428/284; 156/62.8; 156/181; 156/272; 156/296; 428/289; 428/298; 428/299; 428/302; 428/535; 428/537; 428/913
[58] Field of Search ............... 428/236, 245, 288, 297, 428/298, 299, 302, 303, 364, 393, 537, 198, 535, 284; 156/290, 272, 62.2, 62.8, 306, 181, 296

[56] References Cited

U.S. PATENT DOCUMENTS 3,973,067  8/1976  Newman ............................ 428/288
4,012,281  3/1977  Mayer et al. ........................ 428/303

Primary Examiner—James J. Bell

[57] ABSTRACT

A high loft, low density, nonwoven fibrous material is provided comprising two layers of irregularly arranged, intersecting, overlapping, mechanically interengaged, loosely assembled fibers, one of the layers including thermoplastic synthetic wood pulp fibers at least in the portion thereof at the interface to the other layer, at least some of the thermoplastic synthetic wood pulp fibers in the one layer being in contact with and fused with segments of fibers of said other layer.

The material is produced by air-laying the aforementioned layers successively so that some thermoplastic synthetic wood pulp fibers in one layer are in contact with some fibers in the other layer, and then applying heat without pressure to fuse and bond at least some of the thermoplastic synthetic wood pulp fibers in one layer to fibers in the other layer.

40 Claims, 13 Drawing Figures

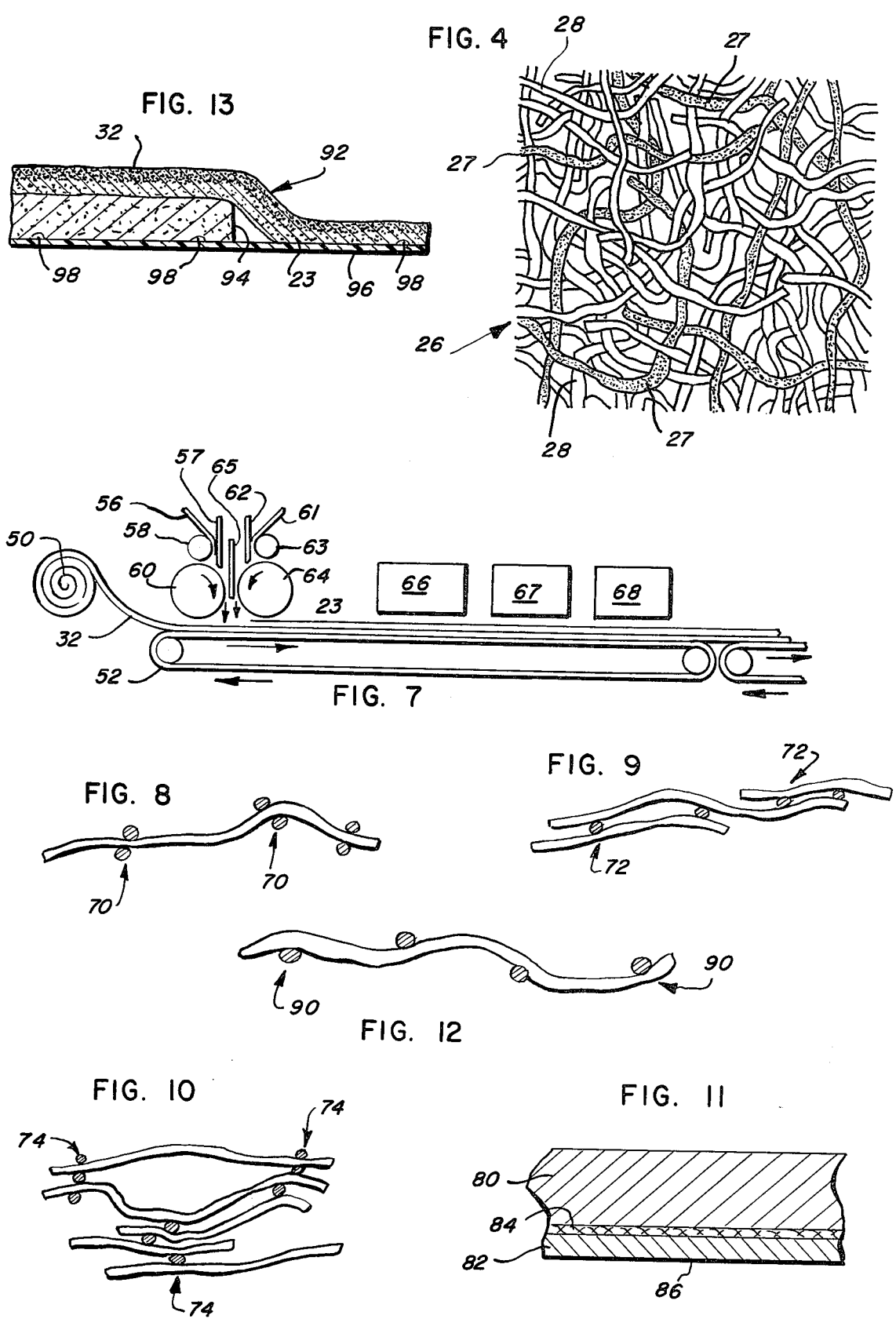

FIBROUS MATERIAL AND METHOD OF MAKING THE SAME

This application relates to a high loft, low density, nonwoven fibrous material, such as an air-laid web or fabric, having synthetic wood pulp fibers located at at least a midportion thereof parallel to or including its median plane, and to a method of producing such a material.

BACKGROUND OF THE INVENTION

Synthetic polymeric fibers that have physical and morphological characteristics generally similar to wood pulp fibers produced from natural woods have been known for approximately 10 years. Examples of such fibers are the synthetic wood pulp fibers formed of polyethylene that are sold by Crown Zellerbach under the trademark SWP.

Various methods of making synthetic wood pulp fibers are known, including (1) solution polymerization accompanied by stirring, (2) dissolving a preformed polymer and subjecting the solution to an anit-solvent, or (3) forming the polymer at the interface between liquid layers, with localized stirring provided to pull the polymeric material thus produced into fibrillated forms. Examples of methods of producing synthetic wood pulp fibers are disclosed in U.S. Pat. Nos. 3,560,318; 3,081,519; 3,003,912; 3,068,527; and 3,290,207; South African Pat. No. 697,431; United Kingdom Pat. No. 1,102,342; and Netherlands Patent Application No. A132/48-7313178.

As used in this specification and the appended claims, the term "synthetic wood pulp fibers" means synthetic, water dispersible, thermoplastic, elongated, supple, randomly bent, polymeric fibers or fibrils generally similar in size and shape to conventional wood pulp fibers produced from naturally occurring woods. Each such "synthetic wood pulp fiber" is of irregular cross sectional shape measured at any given point along its length, and in addition is non-uniform in cross section along its length. The predominant shape of the fibers is usually rather ribbon-like.

The present invention utilizes synthetic wood pulp fibers in a high loft, low density, nonwoven fibrous material such as an air-laid web or fabric. Nonwoven materials are structures which consist of an assemblage or web or irregularly arranged fibers, joined randomly or more or less systematically by mechanical, chemical or other means. These materials are well known in the art, having gained considerable prominence within the last twenty years or so in the consumer market, the industrial commercial market and the hospital field. For example, nonwoven materials are becoming increasingly important in the textile and related fields, one reason being because of their low cost of manufacture for a given coverage as compared to the cost of more conventional textile fabrics made by weaving, knitting or felting. Typical of their use is the production of hospital caps, dental bibs, eye pads, dress shields, shoe liners, shoulder pads, skirts, hand towels, handkerchiefs, tapes, bags, table napkins, curtains, draperies, diaper facings, underpads, hospital drapes, and the like. Generally speaking, nonwoven materials are available today in a wide range of fabric weights of from as little as about 100 grains/sq. yd. to as much as about 4,000 grains/sq. yd. or even higher.

A number of processes and types of apparatus are known for producing nonwoven materials. These include (1) mechanical techniques (e.g. carding or garnetting), (2) wet laying techniques (e.g. inclined wire paper apparatus, cylinder paper apparatus, etc), and (3) air-laying techniques. The high loft, low density, nonwoven materials such as webs or fabrics to which this invention relates may suitably be produced, in the manner to be explained in detail below, from layers of material manufactured by well-known air-laying processes.

SUMMARY OF THE INVENTION

In the method of this invention, a first layer of irregularly arranged, intersecting, overlapping, mechanically interengaged, loosely assembled fibers is brought together with a second layer of similarly disposed fibers that includes synthetic wood pulp fibers in portions of the layer that are immediately adjacent the first layer, when the two layers are brought together. This brings at least some of the synthetic wood pulp fibers of the second layer into contact with fibers of the first layer. Both layers include a multiplicity of interstices between their respective fibers, at least some of the interstices of the first layer being of a width at least two times as wide as the mean diameter of the synthetic wood pulp fibers of the second layer, and at least some of the interstices of the second layer at least two times as wide as the mean diameter of the fibers of the first layer.

In one form of the method of this invention, the second layer containing synthetic wood pulp fibers is supported as a base layer, with one of its surfaces exposed for positioning of other fibers thereon. The second layer may or may not be self-supporting, as desired. In this form of the method, the first layer is positioned upon the exposed surface of the base layer, to bring at least some of the synthetic wood pulp fibers in this second layer into contact with fibers of the first layer. Or, if desired, the second layer containing synthetic wood pulp fibers may be positioned upon the first fibrous layer, either self-supporting or not, as a base layer.

Whichever method is used, because of the supple nature of synthetic wood pulp fibers, it would be expected that substantially all such fibers in the second fibrous layer that are positioned in contact with fibers of the first layer would be matted down against the fibrous first layer. For it would be expected that the contact between fiber segments in the first layer and fiber segments of synthetic wood pulp in the second layer would tend to be of the type in which one fiber segment lies either parallel to or at an angle to another fiber segment on top of that other fiber, with the areas of contact thus being essentially only two-dimensional because confined to the precise interface between the two layers. Consequently, even though it is well known that synthetic wood pulp fibers are thermoplastic and can serve to bond various layers of material to each other under heat and pressure (as disclosed, for example, in the section headed "Applications—Nonwovens and Laminates" in the September 1974 publication by Crown Zellerbach entitled SWP), with the areas of contact between layers of loosely assembled fibers being only two-dimensional it would not be expected that heating the regions on either side of the precise interface between the two fibrous layers in the absence of pressure would produce an adequate bond between the synthetic wood pulp fibers of the second layer and the fibrous first layer.

Surprisingly, it has been discovered that excellent delamination resistance is provided when in accordance with this invention the two fibrous layers in contact with each other are heated in the absence of pressure to produce fusing of the synthetic wood pulp fibers that are present in at least the second layer. Apparently, there is in fact sufficient three-dimensional interfiber contact—which extends beyond or bridges the precise interface between the two layers of the fibrous material and into the two layers themselves—to produce a reliable bonding, and resulting resistance to delamination, after heat is applied to the synthetic wood pulp fibers lying in the region on each side of that interface.

The mechanism by which this three-dimensional interfiber contact occurs is believed to vary somewhat depending upon the method by which the first layer is positioned adjacent to and in contact with the second. Among other ways, this positioning may be carried out, for example, (1) by a deposition process, preferably air deposition, in which the first fibrous layer is simultaneously formed and positioned upon the second fibrous layer as a base layer, or (2) if desired, by positioning the first layer as a self-supporting web of fibers upon the second layer.

The reverse order may also be employed, with the second fibrous layer being positioned upon the first, either by an air deposition process, as a self-supporting web, or as a water suspension or latex dispersion of fibers. In the case of air deposition of the second layer upon the first or the application of a water suspension or latex dispersion of fibers to form the second layer, it is believed that the random fall of fibers onto the base layer causes some of the free outer end portions of synthetic wood pulp fibers to protrude downward from the boundary surface of the second layer and insert themselves within the interstices between the fibers of the first layer and come into contact with some of those fibers. When the second layer is positioned upon the first as a self-supporting web, it will in all likelihood have some fiber outer end portions protruding from its external boundary surface, and it is believed that the relative movement of the self-supporting web containing synthetic pulp fibers with respect to the base layer with which it is brought into contact—for example, relative movement produced by vibration of the apparatus upon which the two layers are supported—will tend to cause at least some of the synthetic wood pulp fiber end portions to insert themselves within the interstices between the fibers of the base layer and there contact some of those fibers. The tendency for three-dimensional interfiber contact of these layers to occur in either of these manners as fiber end portions bridge the interface between the fibrous layers is probably facilitated by the fact that short exposed ends of synthetic wood pulp fibers extending out of the boundary surface of the second layer of fibers are less pliant and supple than are segments of the same fibers in longer lengths.

Whatever method is used to bring fibers of the first and second fibrous layers into contact with each other, heating the end portions of synthetic wood pulp fibers of the second layer that extend into the first layer within interstices of that layer to contact fibers of that layer causes the synthetic wood pulp fibers to fuse to each other and to the other fibers present in the first layer. Heating the end portions of fibers of the first layer that extend into the second layer within interstices of that layer to contact synthetic wood pulp fibers lying entirely within the second layer causes at the same time further fusing of fibers of the first and second layers. The result is to form a mechanically stable fibrous material with synthetic wood pulp fibers acting as a binder at least in the regions which are adjacent the interface between the two layers, and are parallel to or include the median plane of the material.

Another surprising aspect of the method of this invention is the fact that a reliable bonding between the two fibrous layers being treated can be achieved with a much lower proportion by weight of synthetic wood pulp fibers than is ordinarily required when other meltable fibers are used to produce fusion bonding. With a homogenously blended nonwoven fabric, 40 percent or more by weight of thermoplastic fibers is usually required for reliable fusion bonding of one fibrous layer to another. It has been discovered that with the method of this invention, which utilizes synthetic wood pulp fibers, the total quantity of such fibers required for a reliable bond between layers may be as low as 10 percent by weight of a homogenously blended layer.

Thus, one feature of the invention is that in the second fibrous layer synthetic wood pulp fibers that are mechanically interengaged with other fibers in that layer are present, at the boundary surface of the layer that is brought into contact with the first fibrous layer, in a quantity sufficient to occupy at least about 10 percent of the area occupied by exposed fiber segments contained in the second layer at that boundary surface. Improved results are obtained when this percentage is at least about 15 percent, and it is preferred that it be at least about 20 percent.

The fibrous first layer of the method of this invention may be unbonded or bonded, as desired, before it is joined to the second fibrous layer. In any case, adding a latex binder both to the first layer and to the second layer of fibers, after they have been bonded together by heat fusion of the synthetic wood pulp fibers as described, produces a fibrous material of great stability and mechanical integrity, with an excellent resistance to abrasion and delamination, without any of the loss of hand or softness that would be expected from the double bonding effect of first the heat fusion of the synthetic wood pulp fibers, and then the addition of a binder.

Either or both of the first and second fibrous layers of the product of this invention may contain textile length fibers (approximately $\frac{1}{4}$ to $1\frac{1}{2}$ or 2 inches) as well as natural wood pulp fibers and synthetic wood pulp fibers of papermaking lengths (approximately 1/16 to $\frac{1}{4}$ inch).

Satisfactory nonwoven fibrous materials may be produced according to this invention weighing between about 100 grains/sq. yd. and about 1200 grains/sq. yd. or even higher.

The fibrous first layer in the method of this invention may be, for example, a web, a nonwoven fabric, or other layer or assemblage of irregularly arranged, loosely assembled fibers. Since at least some interstices must be present in the first layer having a width at least two times as large as the mean diameter of the synthetic wood pulp fibers in the second layer, the first fibrous layer cannot be a compacted or felted layer of fibers.

It is also important for best results that the fibers of the first layer have a melting point that is higher by at least 10° or 20° C. than that of the synthetic wood pulp fibers of the second layer.

The high loft, low density fibrous material of this invention may be used for any purpose for which high loft non-woven products are used but are particularly useful in applications where resistance to delamination is essential, such as in underpads, wet and dry wiping cloths, coverings for sanitary napkins and facings for diapers, particularly where cut edges of the material are exposed rather than being rolled or folded for protection against delamination.

BRIEF DESCRIPTION OF THE DRAWING

The invention will now be described with reference to the accompanying drawing, in which:

FIG. 4 is an enlarged diagrammatic representation of a portion of a second layer of irregularly arranged, loosely assembled fibers that is one component of the product of this invention, in which synthetic wood pulp fibers are intermingled with natural wood pulp fibers;

FIG. 7 is a diagrammatic side elevation view of one form of apparatus for producing the fibrous material of this invention;

FIGS. 8 through 10 are fragmentary, diagrammatic representations in cross section of certain embodiments of the second fibrous layer that is one component of the fibrous material of this invention;

FIG. 11 is a fragmentary, diagrammatic representation in cross section of an embodiment of a high loft, low density, nonwoven fibrous material according to the present invention;

FIG. 12 is a fragmentary, diagrammatic representation in cross section of the second fibrous layer of another embodiment of the fibrous material of this invention; and FIG. 13 is a partial cross section of a typical diaper utilizing the material of this invention as a facing layer.

DETAILED DESCRIPTION OF THIS INVENTION

Starting Materials

Types of Fibers

Figure 1:
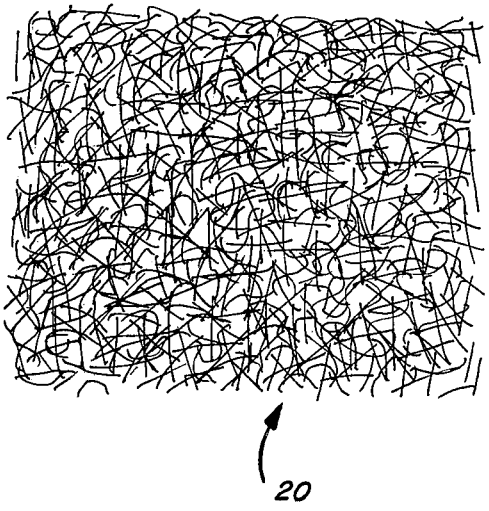
FIG. 1 is a diagrammatic representation of a portion of a first layer of irregularly arranged, loosely assembled fibers that contains no synthetic wood pulp fibers and may be one component of the fibrous material of this invention.

FIG. 1 is a diagrammatic representation of a first layer 20 of irregularly arranged, intersecting, overlapping, mechanically interengaged, loosely assembled fibers defining interstices therebetween which is one component of the product of this invention. The term "mechanically interengaged" is used in this specification and claims to refer to fibers (usually randomly bent) that are interlocked or interentangled with other fibers to provide a degree of structural integrity whether or not binder is present in the layer of fibers.

The fibers of fibrous layer 20 may comprise natural fibers such as cotton, flax, silk, wool, wood pulp, jute, etc.; mineral fibers such as glass; artificial fibers such as viscose rayon, ethyl cellulose or cellulose acetate; synthetic fibers such as polyamides, polyesters, acrylics, vinylidene chloride, polyvinylchloride, polyurethane, etc., alone or in combination with one another. The melting point or degradation temperature of these fibers must be higher, preferably by as much as 10° to 20° C., than the melting point of the synthetic wood pulp fibers contained in the second fibrous layer of the product of this invention. The fibers represented by the drawing of FIG. 1 are approximately ¼ inch to ½ inch viscose rayon fibers.

Relatively long textile type fibers above normal paper making lengths and close to normal textile length, say of about ⅜ to 2 inches or longer, are preferred for some applications. Shorter fibers below ¼ inch in length and within the paper making range may be used in other applications. It is preferred, however, that any shorter paper making fibers employed be unbeaten or substantially unhydrated if a textile-like fibrous material is desired as the end product. Shorter wood fibers may be used to decrease the cost of the product of this invention, with longer fibers intermixed therewith to provide the strength desired in the resulting product.

Figure 2:
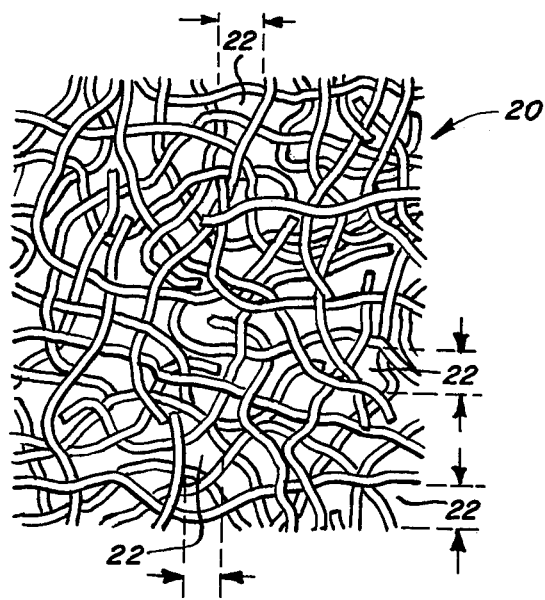
FIG. 2 is an enlarged diagrammatic representation of the fibrous material of FIG. 1.

FIG. 2 is a diagrammatic repesentation giving an enlarged view of first fibrous layer 20 of FIG. 1, and the fibers shown in the figure are thus again ¼ inch to ½ inch viscose rayon fibers. In FIG. 2 the fibers are disposed in the same manner as in the fibrous layer of FIG. 1, with the fibers defining interstices 32 between adjacent fibers of the layer. Some interstices in fibrous layer 20 are quite small, but at least some of the interstices between fibers in the layer, as shown in FIG. 2, have a width at least twice as large as the mean diameter of the fibers that make up second fibrous layer 32 to be described below.

Figure 3:
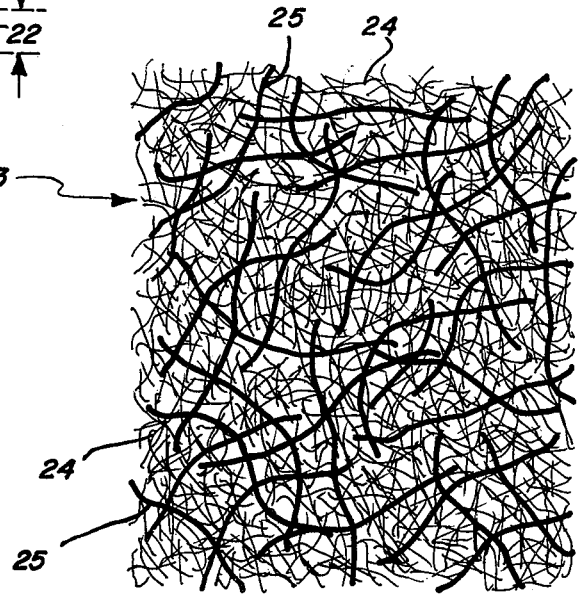
FIG. 3 is a diagrammatic representation of a portion of another layer of irregularly arranged, loosely assembled fibers, including textile length fibers but no synthetic wood pulp fibers, that may constitute the first layer of the fibrous material of this invention.

FIG. 3 is another diagrammatic representation of a first fibrous layer 23 for use in the method of this invention. In this fibrous layer, shorter fibers 24, approximately ¼ to ½ inch in length, are intermixed with longer fibers 25 (shown as dark fibers in FIG. 3) which are about 1 to 2 inches in length.

FIG. 4 is a diagrammatic representation of a second layer 26 of irregularly arranged, loosely assembled fibers comprising one component of the product of this invention. In this embodiment, synthetic wood pulp fibers 27 (stippled in the drawing) are intermingled with natural wood pulp fibers 28.

If desired, fibrous layers 20, 23 and 26 may be formed by means of an air deposition process.

Fiber Disposition

Figure 5:
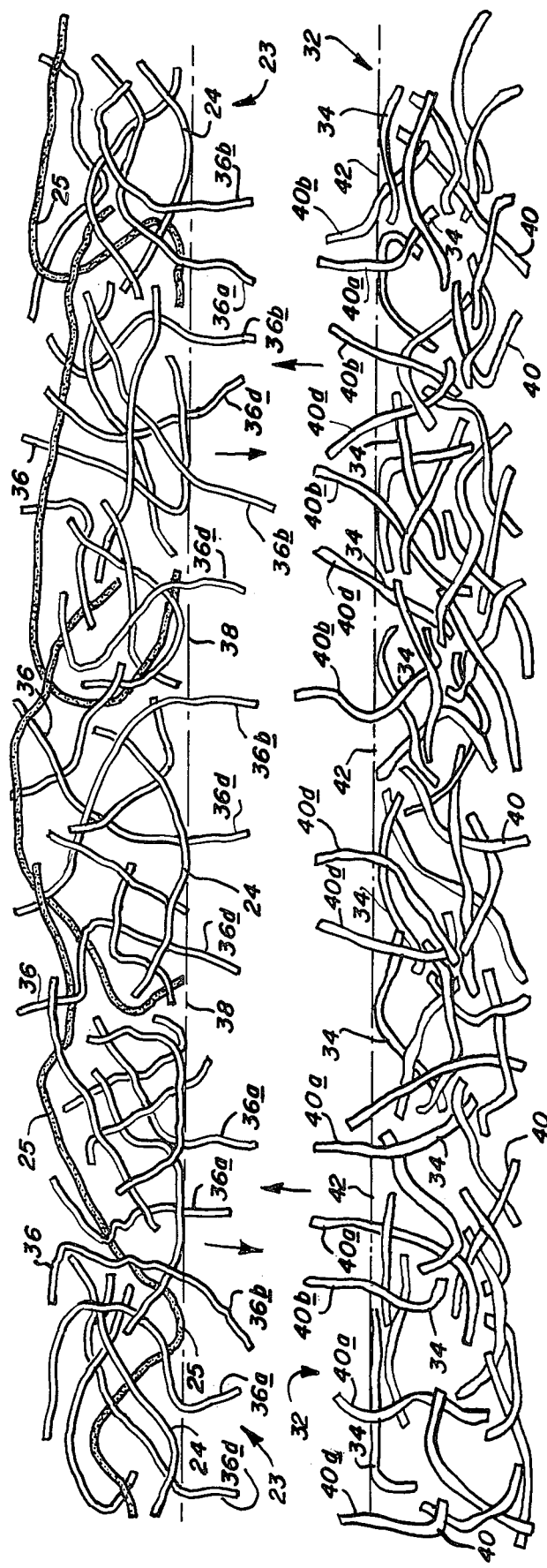
FIG. 5 is an enlarged diagrammatic representation in cross section of the first fibrous layer of FIG. 3 being brought together in the first step of the method of this invention with a second layer of synthetic wood pulp fibers that is positioned below it.

FIG. 5 is a diagrammatic representation of an enlarged cross sectional view of first fibrous layer 23 of FIG. 3, shown being brought together in the first step of the method of this invention with second fibrous layer 32 that is positioned below it. First fibrous layer 23 contains shorter fibers 24 and longer fibers 25 (stippled in FIG. 5) intermingled therewith.

Loosely assembled fibers 24 and 25 of first fibrous layer 23 are irregularly arranged, intersecting, overlapping and mechanically interengaged with each other. The term "mechanically interengaged" is used in this specification and claims to refer to fibers (usually randomly bent) that are interlocked or interentangled with other fibers to provide a degree of structural integrity whether or not any binder is present in the layer of fibers.

In the embodiment shown, second fibrous layer 32 is constituted of synthetic wood pulp fibers 34, which are disposed in a similar manner to fibers 24 and 25 of first fibrous layer 23. This includes the fact that synthetic wood pulp fibers 34 form interstices between individual fiber segments some of which interstices have a width at least twice as large as the mean diameter of the fibers that make up fibrous layer 23. Fibers 34 have an average length of about ¼ inch.

External Boundary Surface

As is seen from FIG. 5, the greater part of the fibrous mass that comprises first fibrous layer 23 lies within the interior of the fibrous structure as a whole. In fact, in the case of a number of the fibers the individual fiber lies within the interior of the fiber structure for the entire fiber length. However, a number of fibers of layer 23 have free fiber ends 36 extending outwardly from at least one boundary surface of the layer.

In FIG. 5, a substantial number of free fiber ends 36 extend downwardly from plane 38, which is the effective lower boundary surface of fibrous layer 23 as the layer is being moved into position on second fibrous layer 32 below it. Second fibrous layer 32 likewise has free fiber ends 40 extending outwardly from the layer. In FIG. 5, a substantial number of free fiber ends 40 extend upwardly from the plane of upper boundary surface 42 of layer 32.

In the embodiment under discussion, all the fibers 34 present at upper boundary surface 42 of second fibrous layer 32 are synthetic wood pulp fibers, and all these fibers are mechanically interengaged with other fibers 34 in layer 32. Satisfactory results are contained when synthetic wood pulp fibers 34 mechanically interengaged with other fibers in second layer 32 are present at boundary surface 42 in a quantity sufficient to occupy at least about 10 percent of the area occupied by exposed fiber segments of all kinds contained in layer 32 at the boundary surface in question.

Figure 6:
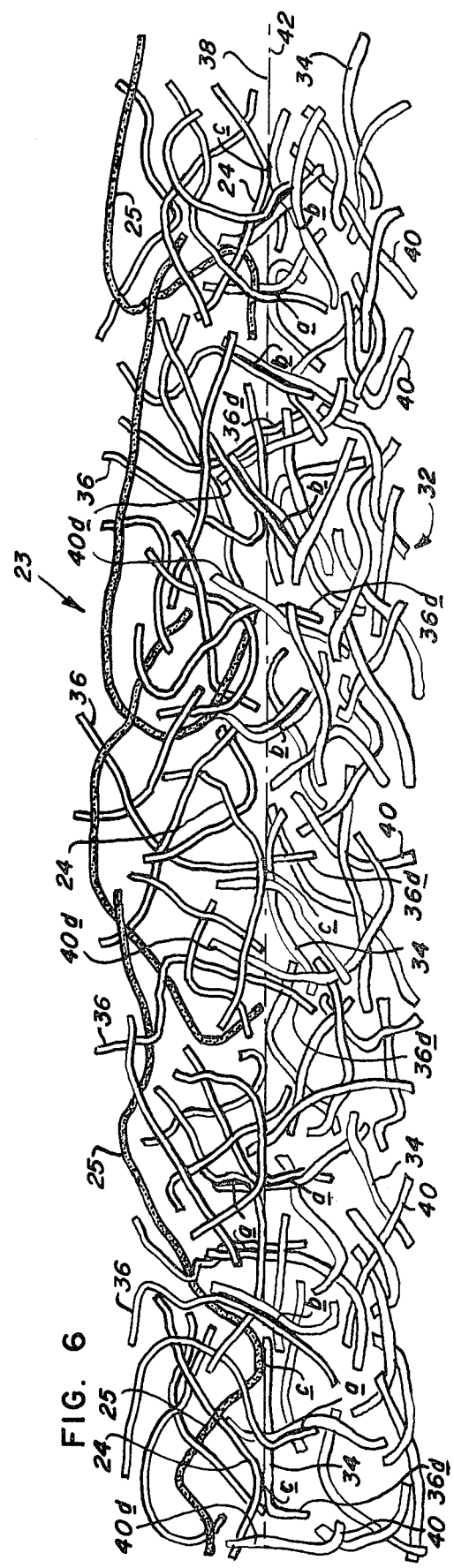
FIG. 6 is a diagrammatic representation in cross section of the fibrous material formed by bringing together the two fibrous layers of FIG. 5.

Improved results are obtained when this percentage is at least about 15 percent, and still further improvement when the percentage is at least about 20 percent. The greatest possible bonding that can be achieved with the method of this invention results from the use, as depicted in FIGS. 5 and 6, of a second fibrous layer 32 that consists entirely of synthetic wood pulp fibers.

First Step of Method

Bringing Fibrous Layers Together

In the first step of the method of this invention, first fibrous layer 23 and second fibrous layer 32 are brought together as illustrated, for example, in FIG. 5. In the embodiment shown, second layer 32 consisting of synthetic wood pulp fibers 34 is supported as a base layer with boundary surface 42 exposed for positioning the fibers of first layer 23 upon it. First fibrous layer 23 is positioned upon base layer 32, as illustrated in FIGS. 5 and 6, in the form of a self-supporting web of fibers, which may be already bonded, or unbonded, as desired.

In a continuous method according to this invention, fibrous layers 23 and 32 may be moved from left to right in FIG. 5 as they are being brought together in the first step of this invention. They may continue to move from left to right in FIG. 6 after first fibrous layer 23 has come to rest on second fibrous layer 32. For example, layer 32 and the combined layers 23 and 32 in FIGS. 5 and 6, respectively, can be supported on the upper reach of an endless belt that moves from left to right in these two figures.

Since any moving apparatus upon which layers 23 and 32 are supported in this way will inevitably have some degree of vibration due to the moving parts of the apparatus, there will be some relative movement between the two fibrous layers 23 and 32 as they are being brought together and moved on through the apparatus. This will tend to cause at least some of the synthetic wood pulp fiber end portions 40 extending upward from the boundary surface 42 of fibrous layer 32 to insert themselves within the interstices between fibers 24 and 25 of layer 23. At the same time, the relative movement between fibrous layers 23 and 32 will tend to cause at least some of fiber end portions 36 to insert themselves within the interstices between fibers 34 of second, lower fibrous layer 32. As this happens, synthetic wood pulp fiber segments in layer 32 come into contact with other fiber segments in layer 24 in several ways to be described below.

If desired, first fibrous layer 23 shown in FIG. 3 may be deposited upon second fibrous layer 32 containing synthetic wood pulp fibers by forming layer 23, and simultaneously positioning it upon layer 32 as a base layer, by means of an air deposition process. The left-hand portion of FIG. 7 provides a diagrammatic showing in side elevation of apparatus for this form of the method of this invention, similar to the web forming apparatus disclosed in commonly assigned U.S. Pat. Nos. 3,740,797 to Farrington, 3,768,118 to Ruffo et al., and 3,772,739 to Lovgren.

In FIG. 7, second fibrous layer 32 consisting in whole or in part of synthetic wood pulp fibers is fed from supply roll 50 onto the upper reach of endless belt 52, which is moving from left to right as shown. At the same time, first fibrous layer 23, such as shown in FIG. 3, is simultaneously formed and deposited upon second fibrous layer 32, to move from left to right with layer 32 while interfiber contact such as described below in some detail in connection with FIG. 6 is produced.

Natural wood pulp fibers 24 and textile length fibers 25 (FIG. 3) are deposited by air deposition apparatus 54 on second fibrous layer 32 to form first fibrous layer 23. Wood pulp board 56 is fed into apparatus 54 between guide plate 57 and feed roll 58, into edgewise contact with lickerin 60, which breaks the board up into individual natural wood pulp fibers. At the same time, a supply of textile length fibers in the form of carded web 61 is fed between guide plate 62 and feed roll 63 into lickerin 64, and from there the fibers are directed onto fibrous layer 32 where they are intermingled with the natural wood pulp fibers deposited thereon as just described. The vertical location of baffle 65 determines the degree of crossover, or the relative proportions of short fibers 24 and longer fibers 25 that are deposited at each thickness level to form fibrous layer 23.

The resulting fibrous material made up of two components, first fibrous layer 23 and second fibrous layer 32, is carried to the right by endless belt 52 in FIG. 7 for further treatment by application of heat.

Interfiber Contact

When fiber end portions 36 and 40 that extend outwardly beyond their respective boundary surfaces 38 and 42 penetrate the opposing fibrous layer as layers 23 and 32 are brought together in the first step of this invention, considerable contact is effected between fiber segments of synthetic wood pulp fibers in second layer 32 and fibers of first layer 23. The resulting interfiber contact—with fiber segments of synthetic wood pulp fibers 34 of second fibrous layer 32 resting in contact with first fibrous layer 23 after either free fiber ends 36 or 40, or some of both, have inserted themselves into interstices between the fibers of the other layer—is illustrated in FIG. 6 in diagrammatic fashion. FIG. 6 is not intended to suggest that the precise types of contact zones shown there are necessarily identifiable in the product of this invention, but the contact zones shown are intended to suggest some considerable degree of contact between the fibers in question.

It may happen that some exposed fiber end portions 36a and 40a as shown in FIG. 5 will move into contact with each other as seen in FIG. 6 when fibrous layers 23 and 32 are brought together in the first step of the method of this invention. Contact zones of this type are indicated by the letter "a" in FIG. 6 at several locations in the left-hand portion of the figure, and also in the right-hand portion.

In some cases, outwardly extending fiber end portions 36b and 40b may collide with each other as fibrous layers 23 and 32 are brought together, and be bent into positions where they maintain fiber contact. Such fiber contact is indicated by the letter "b" in the left-hand portion, the middle, and the right-hand portion of FIG. 6.

The interfiber contact thus far described is believed to provide the major portion of the structural integrity of the fibrous material of this invention. The contact described may in some instances be further supplemented by an actual "intermeshing" of exposed fiber end portions with one fiber end sliding behind another fiber end to provide not only fiber contact but a more positive engagement somewhat similar to the mechanical interengagement or interentanglement of the bent fibers that is present throughout the body of fibrous layers 23 and 32. However, it is believed that the incidence of such intermeshing of fiber ends is typically not very high.

Another type of interfiber contact of less importance, but still adding to the structural integrity of the fibrous material of this invention, is the essentially two-dimensional contact of parallel fiber segments lying at the respective boundary surfaces 38 and 42 of fibrous layers 23 and 32 when they are brought together. Examples of this supplementary interfiber contact are shown at "c" at the left-hand side, the middle, and the right-hand side of FIG. 6.

Some exposed and protruding fiber end portions 36d and 40d fail to make contact with any fibers in the opposing fibrous layers. Examples of such situations are shown at the left-hand end, and at several places near the middle, of FIG. 6.

Second Step of Method

In the second step of the method of this invention, heat is applied in the absence of pressure at least to the portions of fibrous layers 23 and 32 in which synthetic wood pulp fibers 34 of layer 32 are in contact with fibers 24 and 25 of layer 23, to raise the temperature of fibers 34 to or a little above the melting point of the synthetic wood pulp fibers. In other words, heat as described is applied at least to the fibrous regions in which contact zones, a, b, and c in FIG. 6 are located. As a result, some or all of synthetic wood pulp fibers 34 that are in contact with fibers of first fibrous layer 23 are fused and bonded to the latter fibers, to produce a fibrous material of good stability and mechanical integrity, excellent resistance to delamination, and good hand and softness.

As indicated, heat is applied during this second step at least to the portions of layers 23 and 32 that lie immediately adjacent interface 38/42 located between them. The remaining portions of the fibrous material produced by the method of this invention may, if desired, also be subjected to heat in the absence of pressure, and this will be particularly useful if synthetic wood pulp fibers are distributed in other portions of the fibrous material in addition to those immediately adjacent interface 38/42.

The right-hand portion of FIG. 7 shows diagrammatically means for applying heat to fibrous layers 23 and 32. Heating means 66, which may be a dielectric heater, infra-red heater, radiant heater, or other heating means, applies heat to the two fibrous layers supported on endless belt 52, as they move to the right in FIG. 7. The resulting heat fusing and bonding of synthetic wood pulp fibers to other fibers of the product produces a firm, reliable engagement between fibrous layers 23 and 32.

Synthetic wood pulp fibers 34 in second layer 32 should have a melting point lower than the melting point or degradation temperature of every other type of fibers contained in layers 23 and 32. Preferably, the melting point of the synthetic wood pulp fibers should be at least 10° to 20° C. lower than the melting point of the other fibers.

Additional bonding may be provided, if desired, by depositing adhesive binder on fibrous layers 23 and 32 from applicator means 67 shown diagrammatically in FIG. 7. Applicator means 67 is typically a source of binder coupled with a suction box. Alternatively, applicator means 67 may comprise spray apparatus for the application of binder in the form of droplets. Typically, the amount of binder applied by suction equipment leaves about 2-15% of dry binder residue in the web based on the fiber weight therein and the amount applied by spray equipment leaves about 2-25% by weight of dry binder residue on the same basis.

The binder is preferably distributed throughout both layers. After its introduction into the two layers, the adhesive binder is activated by drying and/or heating, which can be supplied by diagrammatically shown means 68. At least a portion of the heating should preferably be effected by use of heating means, such as a radiant heater, that applies heat to all portions, including the midportions, of the material being produced, in order to avoid undue migration of binder to the external surface of the resulting material.

Particular Embodiments of Fibrous Product

A number of specific embodiments of fibrous material, some of which will now be described, can be produced by the practice of this invention. The particular structure of the fibrous material in each case produces characteristics that make the materials especially useful for certain applications.

In the particular embodiment of the second fibrous layer of this invention that is illustrated in FIG. 4, synthetic wood pulp fibers 27 are arranged in overlapping contact engagement with other synthetic wood pulp fibers in layer 26 to trace a multiplicity of continuous fiber paths extending from one edge of layer 26 to the opposite edge in a generally transverse direction across said material, as from left to right in FIG. 4. In the same way, synthetic wood pulp fibers 26 in overlapping contact engagement with each other trace a multiplicity of continuous fiber paths extending from another edge of layer 26 to the edge opposite thereto in a direction generally normal to the first direction, or in other words in the vertical direction in FIG. 4. Such a network of continuous fiber paths can be produced in most cases by including a sufficient quantity of synthetic wood pulp fibers in layer 26, for example at least about 5 percent by weight and preferably at least about 10 percent of the fibers in the layer, that random disposition of the synthetic wood pulp fibers will bring them into an irregularly arranged pattern with the overlapping contact engagement described. When the fibrous material of this invention includes a second layer 26 as just described, a product of great stability and mechanical integrity, with excellent resistance to abrasion and delamination, is achieved.

If desired, a latex binder may be distributed throughout both the first and second layers of the product of this invention to improve the performance characteristics of the product without any of the loss of hand or softness that would be expected from the double bonding effect of first heat fusing the synthetic wood pulp fibers and then adding the binder.

FIGS. 8 through 10 illustrate portions of embodiments of the second fibrous layer of this invention which include a multiplicity of configurations 70, 72 and 74 of segments of synthetic wood pulp fibers that lie in intersecting, overlapping relationship with one another. Each of these configurations of fiber segments is at least three fiber segments in thickness measured perpendicularly to the median plane of the second fibrous layer.

With second fibrous layers having at least the thickness indicated in FIGS. 8–10, such layers may suitably be referred to as a "veneer" upon the first fibrous layer of the material of this invention. FIG. 11 is a diagrammatic showing of the fibrous material of this invention with first fibrous layer 80 connected with second fibrous layer 82 by fibrous region 84 parallel to the median plane of the material, where synthetic wood pulp fibers are heat fused and bonded with other fibers of the material to provide good structural integrity for the product. As shown, veneer layer 82 is a minor fraction of the thickness of first fibrous layer 80.

Exposed boundary surface 86 of second fibrous layer 82 in the embodiment of FIG. 11, which surface is remote from first layer 80, may contain a quantity of synthetic wood pulp fibers sufficient to provide good abrasion resistance. Satisfactory results are obtained if synthetic wood pulp fibers are present at boundary surface 86 in a quantity sufficient to constitute at least about 10 percent by weight of the fibers in the portions of the fibrous product adjacent that boundary surface. Improved results are achieved if this percentage figure is at least about 15 percent by weight, and still further improvement is achieved with a percentage figure at least about 20 percent by weight.

Boundary surface 86 of the embodiment of the fibrous material of this invention shown in FIG. 11 may be made water resistant by including nonwettable synthetic wood pulp fibers in second fibrous layer 82. Increased water resistance is achieved when the only synthetic wood pulp fibers included in the second fibrous layer are nonwettable, and maximum water resistance is achieved if all the fibers of second fibrous layer 82 are nonwettable synthetic wood pulp fibers. Nonwettable synthetic wood pulp fibers are formed of hydrophobic polymers, and in commercial form should be free of any surfactant film or water soluble finishes on the external surface of the fibers. The external surface portions of second fibrous layer 82 of the embodiment of FIG. 11 may also be rendered water resistant by treatment with small quantities of a hydrophobic latex, a water repellent size, or other water repellent chemicals or polymers.

FIG. 12 gives a fragmentary, diagrammatic representation of a portion of the second fibrous layer of another embodiment of the fibrous material of this invention. In this embodiment, a very thin layer of synthetic wood pulp fibers is positioned across a first fibrous layer by "dusting" individual fibers on the surface of the first layer. Some synthetic wood pulp fibers in the resulting layer may lie entirely by themselves, without overlapping any other synthetic wood pulp fibers in the layer. Some may lie over and in contact with other synthetic wood pulp fibers to form configurations such as fiber configurations 90 in FIG. 12. These fiber configurations are made up of fiber segments lying in intersecting, overlapping relationship, with substantially no configuration of fiber segments being more than two fiber segments in thickness measured perpendicularly to the median plane of the fibrous layer that is "dusted" on the first layer. The layer of synthetic wood pulp fibers that is thus formed is extremely thin, but nevertheless, when fused, imparts good abrasion resistance to the final fibrous product.

FIG. 13 shows a partial cross sectional view of a typical diaper utilizing the material of this invention as a facing layer. The diaper is made of three principal elements, specifically facing layer 92, batt 94 and impervious backing sheet 96. The facing layer is made up, as described in connection with FIG. 6, of layers 23 and 32 with the latter containing wood pulp fibers and being the outermost layer of the structure. For illustrative purposes and to distinguish the two, layer 32 is shown in FIG. 13 as more dense than layer 23, but in actuality the densities of the two layers would ordinarily be approximately equal.

Batt 94 is a high loft, low density, air-laid material made of short cellulose fibers derived from wood pulp or cotton linters.

Impervious backing sheet 96 is a plastic film, such as an embossed polyethylene film.

Backing sheet 96 is adhered to the facing layer and to the batt by spaced lengthwise-extending beads of adhesive 98.

The general nature of the backing sheet and the general nature of the batt are well known in the art and typical diaper structures embodying these elements are shown in U.S. Pat. Nos. 3,612,055 and 3,683,916.

The above detailed description of this invention has been given for clarity of understanding only. No unnecessary limitations are to be understood therefrom, as modifications will be obvious to those skilled in the art.

What is claimed is:

1. A method of producing a high loft, low density, nonwoven fibrous material having thermoplastic synthetic wood pulp fibers in at least one region of said material parallel to or including its median plane which comprises:
   bringing together a first layer of irregularly arranged, intersecting, overlapping, mechanically interengaged, loosely assembled fibers defining interstices therebetween, said fibers including fibers other than thermoplastic synthetic wood pulp fibers, said layer of fibers having free fiber ends extending outwardly from at least one boundary surface of the layer, with a second layer of similarly disposed fibers, said second layer including at least thermoplastic synthetic wood pulp fibers and optionally, other fibers, said thermoplastic synthetic wood pulp fibers located at least in surface portions of said layer immediately adjacent said one boundary surface of the first layer and having free fiber ends extending outwardly therefrom, to bring at least some of the fiber segments of thermoplastic synthetic wood pulp fibers of said second layer into contact with said first layer of fibers of inserting free fiber ends from at least one of said layers into interstices between fibers in the other of said layers, thermoplastic synthetic wood pulp fibers that are mechanically interengaged with other fibers in the second layer being present at the boundary surface of said layer adjacent said first layer in a quantity sufficient to occupy at least about 10 percent of the area occupied by exposed fiber segments contained in the second layer at its said boundary surface, at least some of the interstices between fibers of said first layer being of a width at least twice as large as the mean diameter of said thermoplastic synthetic wood pulp fibers in said second layer, at least some of the interstices between fibers of said second layer being of a width at least twice as large as the mean diameter of the fibers in said first layer, said thermoplastic synthetic wood pulp fibers in the second layer having a melting point lower than the melting point or degradation temperature of every other type of fibers contained in said two layers; and applying heat in the absence of pressure at least to the portions of said two fibrous layers in which thermoplastic synthetic wood pulp fibers of said second layer that are in contact with fibers of said first layer are located, to fuse and bond at least some of said contacting thermoplastic synthetic wood pulp fibers to fibers of said first layer and thereby produce a fibrous material of good stability and mechanical integrity, which displays excellent resistance to delamination as well as good hand and softness.

2. The method of claim 1 in which said second layer containing thermoplastic synthetic wood pulp fibers is a base layer supported to expose one boundary surface thereof for positioning of the fibers of said first layer thereon.

3. The method of claim 2 in which said first layer of fibers is simultaneously formed and positioned upon said base layer containing thermoplastic synthetic wood pulp fibers by an air deposition process.

4. The method of claim 2 in which said first layer of fibers is positioned upon said base layer containing thermoplastic synthetic wood pulp fibers in the form of a self-supporting web of fibers, and said two fibrous layers are vibrated as they are supported in contact with each other, to produce relative movement of the respective fibers of said two layers in the plane of the interface between them.

5. The method of claim 1 in which said first layer is a base layer supported to expose one boundary surface thereof for positioning of the fibers of said second layer containing thermoplastic synthetic wood pulp fibers thereon.

6. The method of claim 5 in which said second layer of fibers containing thermoplastic synthetic wood pulp fibers is simultaneously formed and positioned upon said base layer by an air deposition process.

7. The method of claim 5 in which said layer of fibers containing thermoplastic synthetic wood pulp fibers is positioned upon said base layer in the form of a self-supporting web of fibers, and said two fibrous layers are vibrated as they are supported in contact with each other, to produce relative movement of the respective fibers of said two layers in the plane of the interface between them.

8. The method of claim 1 in which fibers of thermoplastic synthetic wood pulp in said second layer that is brought together with said first layer in the first step of said method are arranged in overlapping contact engagement with other synthetic wood pulp fibers in said second layer to trace a multiplicity of continuous fiber paths extending from one edge of said second layer to the opposite edge in a generally transverse direction across said material, sas well as a multiplicity of continuous fiber paths extending from another edge of said layer to the edge opposite thereto in a direction generally normal to said first direction.

9. The method of claim 8 in which said thermoplastic synthetic wood pulp fibers in said second layer that is brought together with said first layer in the first step of said method include a multiplicity of configurations of fiber segments in in which said segments lie in intersecting, overlapping relationship with one another, each of said configurations being at least three fiber segments in thickness measured perpendicularly to the median plane of said second layer.

10. The fibrous material of claim 9 in which the thickness of said second layer that is brought together with said first layer in the first step of said method is a minor fraction of the thickness of said first layer.

11. The method of claim 1 in which substantially all the fibers in said second layer that is brought together with said first layer in the first step of said method are thermoplastic synthetic wood pulp fibers, and said thermoplastic synthetic wood pulp fibers are substantially free of configurations of fiber segments in which said segments lie in intersecting, overlapping relationship more than two fiber segments in thickness measured perpendicularly to the median plane of said second layer.

12. The method of claim 1 in which thermoplastic synthetic wood pulp fibers that are mechanically interengaged with other fibers in said second fibrous layer are present at the boundary surface of said layer that is adjacent said first layer, when the second layer is brought together with it in the first step of said method, in a quantity sufficient to constitute at least about 15 percent of the area occupied by exposed fiber segments contained in said second layer at said boundary surface.

13. The method of claim 1 in which thermoplastic synthetic wood pulp fibers that are mechanically interengaged with other fibers in said second fibrous layer are present at the boundary surface of said layer that is adjacent said first layer, when the second layer is brought together with it in the first step of said method, in a quantity sufficient to constitute at least about 20 percent of the area occupied by exposed fiber segments contained in said second layer at said boundary surface.

14. The method of claim 1 in which thermoplastic synthetic wood pulp fibers are present in the portions of said second layer at its boundary surface remote from said first layer, when said two layers are brought together in the first step of said method, in a quantity sufficient to constitute at least about 10 percent by weight of the fibers in said remote boundary surface portions, whereby said fibrous material is provided good resistance to abrasion at its said remote surface.

15. The method of claim 1 in which thermoplastic synthetic wood pulp fibers are present in the portions of said second layer at its boundary surface remote from said first layer, when said two layers are brought together in the first step of said method, in a quantity sufficient to constitute at least about 15 percent by weight of the fibers in said remote boundary surface portions, whereby said fibrous material is provided good resistance to abrasion at its said remote surface.

16. The method of claim 1 in which thermoplastic synthetic wood pulp fibers are present in the portions of said second layer at its boundary surface remote from said first layer, when said two layers are brought together in the first step of said method, in a quantity sufficient to constitute at least about 20 percent by weight of the fibers in said remote boundary surface portions, whereby said fibrous material is provided good resistance to abrasion at its said remote surface.

17. The method of claim 1 in which the external boundary surface portions of said first layer that are adjacent said second layer when said two layers are brought together in the first step of said method also contain thermoplastic synthetic wood pulp fibers, at least some of which are mechanically interengaged with other fibers of the first layer, in a quantity equal to at least about 5 percent by weight of the portion of the first layer extending from the innermost thermoplastic synthetic wood pulp fibers to said external boundary surface of the first layer.

18. The method of claim 1 in which nonwettable thermoplastic synthetic wood pulp fibers are included in said second layer that is brought together with said first layer in the first step of said method.

19. The method of claim 1 in which the only thermoplastic synthetic wood pulp fibers included in said second layer that is brought together with said first layer in the first step of said method are nonwettable.

20. The method of claim 1 in which the heating step described therein is carried out by applying radiant heat in the absence of pressure at least to the portions of said first and second layers that lie immediately adjacent the interface between said two layers.

21. The method of claim 20 in which radiant heat is applied in the absence of pressure throughout said two layers.

22. The method of claim 1 in which following said heating step a binder is introduced into said two layers, and is thereafter activated to bond individual fiber segments to each other in both of said layers.

23. The method of claim 22 in which said binder is distributed throughout both said layers.

24. A high loft, low density, non-woven fibrous material of good stability and mechanical integrity, excellent resistance to delamination, and good hand and softness, which comprises a first layer of irregularly arranged, intersecting, overlapping, mechanically interengaged, loosely assembled fibers defining interstices therebetween, said fibers including fibers other than thermoplastic synthetic wood pulp fibers, and a second layer of similarly disposed fibers in firm engagement with said first layer at an interface therebetween, said second layer including, at least thermoplastic synthetic wood pulp fibers and optionally, other fibers, said thermoplastic synthetic wood pulp fibers located at least in portions of said second layer adjacent said interface between said two layers, thermoplastic synthetic wood pulp fibers that are mechanically interengaged with other fibers in said second layer being present in the portions of said layer at said interface between the two layers in a quantity sufficient to occupy at least about 10 percent of the area occupied by fiber segments contained in said second layer at said interface, fibers of at least one of said two layers extending across the interface between the two layers with free end portions of said fibers positioned within interstices between fibers in the other of said layers, at least some of the interstices between fibers of said first layer being of a width at least twice as large as the mean diameter of said synthetic wood pulp fibers in said second layer, at least some of the interstices between fibers of said second layer being of a width at least twice as large as the mean diameter of the fibers in said fiber layer, segments of at least some of the thermoplastic synthetic wood pulp fibers in said second layer being in contact with and heat fused with segments of fibers of said first layer, said thermoplastic synthetic wood pulp fibers in the second layer having a melting point lower than the melting point or degradation temperature of every other type of fibers contained in said two layers.

25. The fibrous material of claim 24 in which thermoplastic synthetic wood pulp fibers of said second fibrous layer extend across the interface between said two layers, with free end portions of said fibers positioned within interstices between fibers in said first layer, where they are in contact with and heat fused with fibers of said first layer.

26. The fibrous material of claim 24 in which fibers of said first fibrous layer extend across the interface between said two layers, with free end portions of said fibers positioned within interstices between fibers in said second layer, where they are in contact with and heat fused with thermoplastic synthetic wood pulp fibers of said second layer.

27. The fibrous material of claim 24 in which thermoplastic synthetic wood pulp fibers in said second layer are arranged in overlapping contact engagement with other thermoplastic synthetic wood pulp fibers in said layer to trace a multiplicity of continuous fiber paths extending from one edge of said material to the opposite edge in a generally transverse direction across said material, as well as a multiplicity of continuous fiber paths extending from another edge of said material to the edge opposite thereto in a direction generally normal to said first direction.

28. The fibrous material of claim 27 in which the thermoplastic synthetic wood pulp fibers in said second layer include a multiplicity of configurations of fiber segments in which said segments lie in intersecting, overlapping relationship with one another, each of said configurations being at least three fiber segments in thickness measured perpendicularly to the median plane of said second layer.

29. The fibrous material of claim 28 in which the thickness of said second fibrous layer is a minor fraction of the thickness of said first fibrous layer.

30. The fibrous material of claim 24 in which substantailly all the fibers in said second layer are thermoplastic synthetic wood pulp fibers, and said thermoplastic synthetic wood pulp fibers are substantially free of configurations of fiber segments in which said segments lie in intersecting, overlapping relationship more than two fiber segments in thickness measured perpendiculary to the median plane of said second layer.

31. The fibrous material of claim 24 in which thermoplastic synthetic wood pulp fibers that are mechanically interengaged with other fibers in said second fibrous layer are present in the portions of said layer at the interface between said two layers in a quantity sufficient to constitute at least about 15 percent of the area occupied by fiber segments contained in said second layer at said interface.

32. The fibrous material of claim 24 in which thermoplastic synthetic wood pulp fibers that are mechanically interengaged with other fibers in said second fibrous layer are present in the portions of said layer at the interface between said two layers in a quantity sufficient to constitute at least about 20 percent of the area occupied by fiber segments contained in said second layer at said interface.

33. The fibrous material of claim 24 in which thermoplastic synthetic wood pulp fibers are present in the portions of said second layer at its external boundary surface remote from the interface between said two layers in a quantity sufficient to constitute at least about 10 percent by weight of said remote boundary surface portions, whereby said fibrous material is provided good resistance to abrasion at its said remote surface.

34. The fibrous material of claim 24 in which thermoplastic synthetic wood pulp fibers are present in the portions of said second layer at its external boundary surface remote from the interface between said two layers in a quantity sufficient to constitute at least about 15 percent by weight of said remote boundary surface portions, whereby said fibrous material is provided good resistance to abrasion at its said remote surface.

35. The fibrous material of claim 24 in which thermoplastic synthetic wood pulp fibers are present in the portions of said second layer at its external boundary surface remote from the interface between said two layers in a quantity sufficient to constitute at least about 20 percent by weight of said remote boundary surface portions, whereby said fibrous material is provided good resistance to abrasion at its said remote surface.

36. The fibrous material of claim 24 in which the portions of said first layer adjacent the interface between said two fibrous layers also contain thermoplastic synthetic wood pulp fibers, at least some of which are mechanically interengaged with other fibers in the first layer, in a quantity equal to at least about 5 percent by weight of the portion of the first layer extending from the thermoplastic synthetic wood pulp fibers located most distant from said interface to said interface.

37. The fibrous material of claim 24 in which both wettable and nonwettable synthetic wood pulp fibers are included in said second layer.

38. The fibrous material of claim 24 in which the only thermoplastic synthetic wood pulp fibers included in said second layer are nonwettable.

39. The fibrous material of claim 24 in which a binder is present in both said first and second layers, said binder bonding individual fiber segments to each other in both of said layers.

40. The fibrous material of claim 39 in which said binder is distributed throughout both said layers.

* * * * *